United States Patent
Lee et al.

(10) Patent No.: US 9,573,915 B2
(45) Date of Patent: Feb. 21, 2017

(54) IONIC LIQUIDS, THE METHOD FOR PREPARING THE SAME AND METHOD FOR REMOVING ACETYLENES FROM OLEFIN MIXTURES USING THE IONIC LIQUIDS

(71) Applicant: KOLON INDUSTRIES, INC., Gyeonggi-Do (KR)

(72) Inventors: Hyun Joo Lee, Gyeonggi-do (KR); Byoung Sung Ahn, Seoul (KR); Hoon Sik Kim, Seoul (KR); Jin-Hyung Kim, Seoul (KR); Gyeong Taek Gong, Seoul (KR)

(73) Assignee: Kolon Industries, Inc., Gyeonggi-do (KR)

( * ) Notice: Subject to any disclaimer, the term of this patent is extended or adjusted under 35 U.S.C. 154(b) by 421 days.

(21) Appl. No.: 14/308,737

(22) Filed: Jun. 19, 2014

(65) Prior Publication Data

US 2014/0296523 A1 Oct. 2, 2014

Related U.S. Application Data

(62) Division of application No. 12/970,346, filed on Dec. 16, 2010, now Pat. No. 8,785,711.

(30) Foreign Application Priority Data

Oct. 4, 2010 (KR) .................. 10-2010-0096389

(51) Int. Cl.
| | | |
|---|---|---|
| *C07D 295/088* | (2006.01) | |
| *C07D 233/60* | (2006.01) | |
| *C07F 1/08* | (2006.01) | |
| *C07C 7/10* | (2006.01) | |
| *C07C 309/68* | (2006.01) | |
| *C07D 207/08* | (2006.01) | |
| *C07D 233/02* | (2006.01) | |

(52) U.S. Cl.
CPC ......... *C07D 295/088* (2013.01); *C07D 233/60* (2013.01); *C07F 1/08* (2013.01); *C07C 7/10* (2013.01); *C07C 309/68* (2013.01); *C07D 207/08* (2013.01); *C07D 233/02* (2013.01)

(58) Field of Classification Search
CPC ....... C07D 295/088; C07D 233/60; C07F 1/08
See application file for complete search history.

(56) References Cited

U.S. PATENT DOCUMENTS

| 3,758,603 | A | 9/1973 | Steigelmann et al. |
|---|---|---|---|
| 4,019,879 | A | 4/1977 | Rabo et al. |
| 4,034,065 | A | 7/1977 | Kasai et al. |
| 4,318,714 | A | 3/1982 | Kimura et al. |
| 4,717,398 | A | 1/1988 | Pearce |
| 6,339,182 | B1 | 1/2002 | Munson et al. |
| 6,623,659 | B2 | 9/2003 | Munson et al. |
| 7,304,200 | B2 * | 12/2007 | Roettger ............... C07B 63/00 585/809 |
| 7,435,318 | B2 | 10/2008 | Arlt et al. |
| 8,110,716 | B2 * | 2/2012 | Lee ....................... C07C 7/10 585/849 |
| 8,143,470 | B2 * | 3/2012 | Ahn ....................... C07C 7/10 585/809 |

FOREIGN PATENT DOCUMENTS

| CA | 2059794 | 8/1992 |
|---|---|---|
| DE | 2 059 794 A1 | 6/1971 |

OTHER PUBLICATIONS

Safarik, D. J. et al., *Olefin/Paraffin Separations by Reactive Absorption: A Review*, Ind. Eng. Chem. Res. 37 (1998) 2571-2581.

* cited by examiner

Primary Examiner — Matthew Coughlin
(74) Attorney, Agent, or Firm — Alston & Bird LLP

(57) ABSTRACT

There are provided an ionic liquid having ether group(s) in which a copper(I) compound is included, a method for preparing the same, and a method for removing traces amounts of acetylene-based hydrocarbon compounds included in olefin by absorption or extraction using the same. When the disclosed solution is used, oxidation of Cu(I) to Cu(II) is prevented since CuX is stabilized by the ionic liquid. Thus, selective removal efficiency of acetylenic compounds is improved greatly while the removal performance is retained for a long period of time. Further, since the solution according to the present disclosure is applicable as an extractant as well as an absorbent, the associated operation is simple and apparatus cost can be decreased.

7 Claims, 1 Drawing Sheet

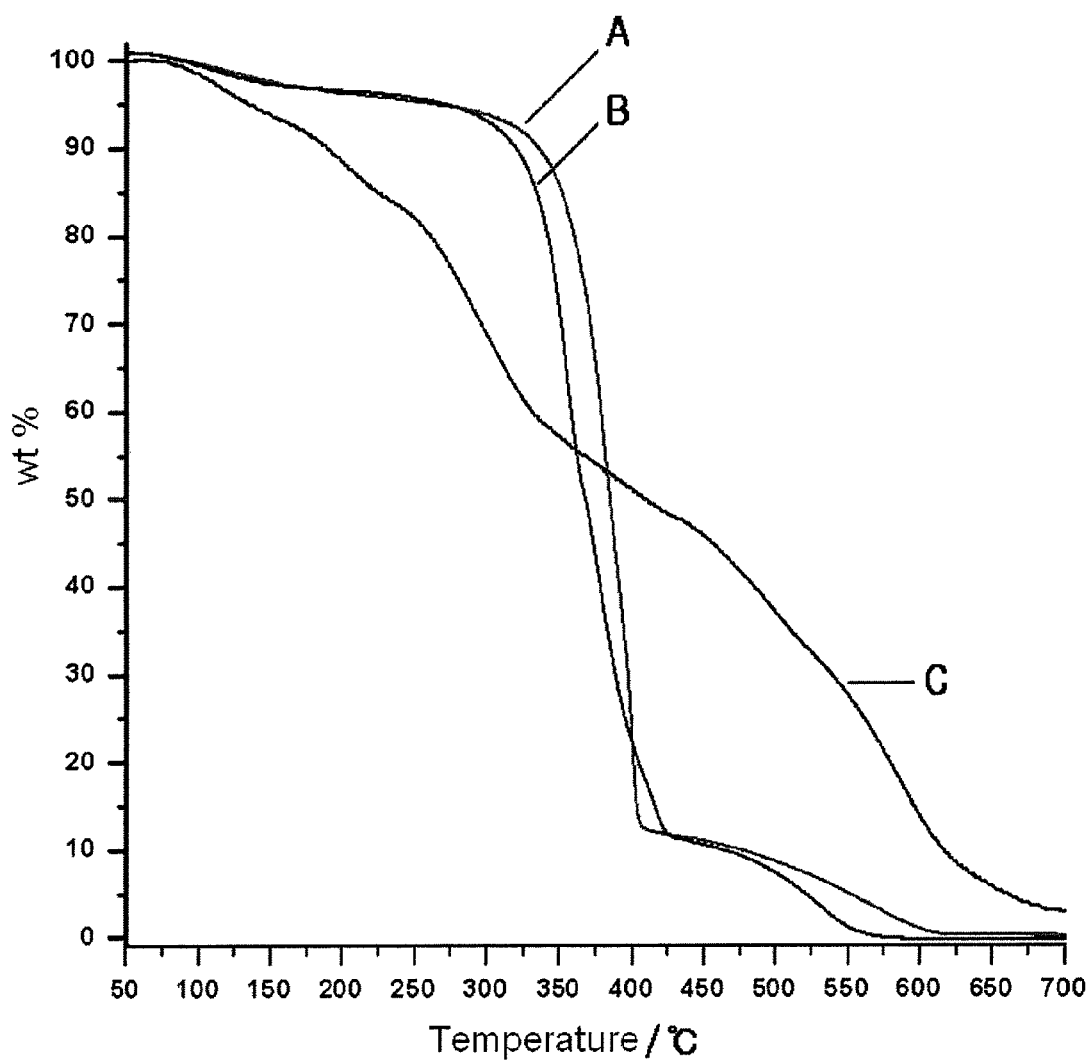

IONIC LIQUIDS, THE METHOD FOR PREPARING THE SAME AND METHOD FOR REMOVING ACETYLENES FROM OLEFIN MIXTURES USING THE IONIC LIQUIDS

CROSS-REFERENCE TO RELATED APPLICATIONS

This application is a divisional of U.S. patent application Ser. No. 12/970,346, filed Dec. 16, 2010, which claims priority under 35 U.S.C. §119 to Korean Patent Application No. 10-2010-0096389, filed on Oct. 4, 2010, in the Korean Intellectual Property Office, each of which is hereby incorporated herein in its entirety by reference.

TECHNICAL FIELD

The present disclosure is related to an ionic liquid, a method for preparing the same and a method for removing acetylenic compounds using the same. More particularly, it relates to the method for effectively removing traces of acetylene-based hydrocarbon compounds included in olefins by absorption or extraction using an ionic liquid containing copper ion.

BACKGROUND

Olefin, one of the major source materials in the chemical industry, is mainly produced by cracking naphtha or natural gas. During this process, paraffinic hydrocarbons and acetylenic compounds having similar boiling points are produced together. Thus, a complicated separation and purification process is required to obtain pure olefins. In particular, the acetylenic compounds acts as a catalytic poison in the polyolefin polyolefin production process, and degrade the quality of the product quality, and is subject to explode or block the fluid flow when converted to solid polyacetylenic compounds and accumulated during the production process. Therefore, the removal of the acetylene compounds is essential.

For practical applications, traces of acetylenic compounds included in olefin are converted into olefins via hydrogenation in the presence of a catalyst. However, olefin produced during the hydrogenation of acetylenic compounds or olefin used as a reagent can react together and form paraffins; this might cause a loss of olefin.

For this reason, a catalyst capable of selectively hydrogenating acetylenes has to be used to remove the acetylenic compounds. Currently, palladium supported on α-alumina is the most frequently used and commercially available catalyst. However severe catalyst poisoning due to excessive paraffin production from high hydrogenation activity and carbon deposition requires an additional regeneration process of the catalyst.

In addition to hydrogenation, low-temperature distillation, liquid absorption, solid adsorption, membrane separation, or the like are known as methods for removing the acetylenic compounds. Among them, low-temperature distillation and liquid absorption are frequently employed to separate unsaturated compounds such as carbon monoxide (CO) or olefin from gaseous mixtures. However, low-temperature distillation requires expensive equipments, and high operation costs. The liquid absorption method using volatile organic solvents such as dimethylformamide (DMF) or N-methylpyrrolidone (NMP) requires an additional separation/purification process of removing olefins from acetylenic compounds dissolved in an absorbent to obtain pure acetylenic compounds because of low selectivity. In addition, loss of the volatile organic solvents during repeated regeneration of the absorbent is economically unfavorable.

U.S. Pat. Nos. 4,019,879 and 4,034,065 disclose methods of removing unsaturated compounds such as CO via adsorption using molecular sieves. However, their adsorption capacity is limited and high temperature and high vacuum is required for degassing. U.S. Pat. No. 4,717,398 discloses a method of removing unsaturated compounds by a pressure swing process using an adsorbent obtained using copper [Cu(I)]-exchanged faujasite zeolite.

German Patent No. 2,059,794 discloses a method of removing unsaturated compounds including acetylene using a liquid absorbent containing a Cu(I) compound and an alkanolamine such as monoethanolamine as main components. However, it requires an additional purification apparatus because of contamination of the final product by the alkanolamine and co-adsorption of olefin. *Ind. Eng. Chem. Res.* 2571 (1998) discloses a method of separating unsaturated compounds from paraffins using a Cu(I) or Ag(I) compound solution reacting reversibly with olefin and acetylene. However, it requires a complicated regeneration process because of low stability of the adsorbent.

U.S. Pat. No. 3,758,603 discloses a method of separating unsaturated compounds from saturated compounds using a liquid barrier prepared by supporting silver salt on a porous separation membrane. The liquid barrier technique is disadvantageous as silver ions are lost by supplied gases and the solvent evaporate easily. As a result, the separation efficiency cannot maintain for a long time. Even when a cation exchange membrane is used to prevent the silver ion loss as described in U.S. Pat. No. 4,318,714, a water content in the separation membrane has to be maintained above a certain level as in the case where an immobilized liquid barrier is used, because the facilitated transport occurs only in the presence of water, and water has to be removed later after the separation. Further, since the separation membrane has to be thick with a thickness of 100 to 500 μm or larger, it is impractical. In addition, the separation efficiency is not satisfactory.

Although the aforesaid methods using the Cu(I) or Ag(I) compound are applicable to the separation of unsaturated hydrocarbons from saturated hydrocarbons, they are inapplicable to the separation of a mixture of unsaturated compounds. It is because the separation selectivity is fairly low since the Cu(I) or Ag(I) compound forms π-complexes having bond strengths comparable to those of double or triple bonds.

SUMMARY

The present disclosure is directed to providing anionic liquid containing copper (Cu) ions capable of effectively removing acetylenic compounds from olefin.

The present disclosure is also directed to providing a method for preparing an ionic liquid containing copper ions capable of removing acetylenic compounds from olefin.

The present disclosure is also directed to providing a method for effectively removing traces of acetylene-based hydrocarbon compounds included in olefin by absorption or extraction using a copper ion-containing ionic liquid, In one general aspect, the present disclosure provides an ionic liquid including one or more organometallic compound(s) represented by Chemical Formula (1), (2) or (3):

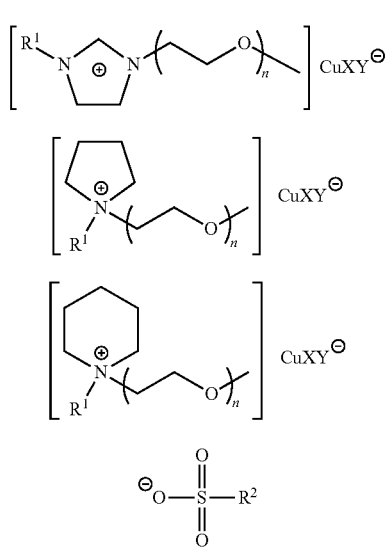

wherein

X is an anion selected from Cl, Br and I, $R^1$ is $C_1$-$C_4$ substituted or unsubstituted alkyl, n is an integer from 1 to 6, and Y is a sulfonate anion represented by Chemical Formula (4), wherein $R^2$ is $C_1$-$C_4$ substituted or unsubstituted alkyl.

In another general aspect, the present disclosure provides a method for preparing an organometallic compound represented by Chemical Formula (1), (2) or (3) by reacting a copper halide represented by Chemical Formulae (5) with a compound represented by Chemical Formula (6), (7) or (8) according to Schemes 1 to 3:

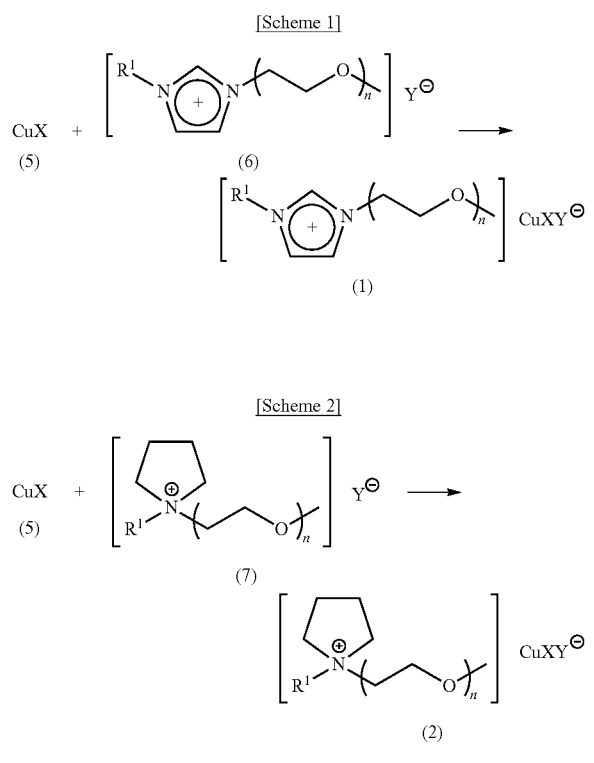

In another general aspect, the present disclosure provides a method for removing acetylenic compounds from an olefin mixture using an ionic liquid including one or more organometallic compound(s) represented by Chemical Formula (1), (2) or (3).

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which:

FIG. 1 compares thermal stability of ionic liquids.

DETAILED DESCRIPTION OF EMBODIMENTS

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is only to describe particular embodiments and is not intended to limit the example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail.

The ionic liquid according to the present disclosure comprises one or more organometallic compound(s) represented by Chemical Formula (1), (2) or (3):

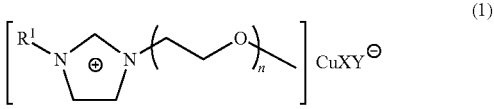

-continued $$\left[\begin{array}{c}\text{(pyrrolidinium with R}^1\text{, }(\text{OCH}_2\text{CH}_2)_n\text{)}\end{array}\right] \text{CuXY}^{\ominus} \quad (2)$$

$$\left[\begin{array}{c}\text{(piperidinium with R}^1\text{, }(\text{OCH}_2\text{CH}_2)_n\text{)}\end{array}\right] \text{CuXY}^{\ominus} \quad (3)$$

$$\begin{array}{c}\ominus\text{O}-\underset{\underset{\text{O}}{\parallel}}{\overset{\overset{\text{O}}{\parallel}}{\text{S}}}-\text{R}^2\end{array} \quad (4)$$

wherein

X is an anion selected from Cl, Br and I, $R^1$ is $C_1$-$C_4$ substituted or unsubstituted alkyl, n is an integer from 1 to 6, and Y is a sulfonate anion represented by Chemical Formula (4), wherein $R^2$ is $C_1$-$C_4$ substituted or unsubstituted alkyl.

In general, a copper halide (CuX) is not dissolved in organic solvents and oxidized by reacting with alcohol or amine. Further, it tends to form explosive acetylides by reacting with acetylenes. In contrast, ionic liquids represented by Chemical Formulae (1) to (3) are not easily oxidized unlike CuX. In addition, they do not form acetylides, because they weakly interact with hydrogen atoms of acetylenic compounds. CuX tends to form strong n-bonds with compounds having double bonds or triple bonds because of its vacant sites, and it is impossible to selectively remove the compounds having triple bonds from the mixture of compounds having double bonds and compounds having triple bonds, because the bonding strength is similar.

In contrast, since [CuXY]$^-$ represented by Chemical Formulae (1) to (3) is already saturated with a ligand, they have no vacant site needed to form n-bonding with compounds having double bonds or triple bonds. Thus, although they weakly bind to the olefin and acetylenic compounds, the basic sulfonate group bound to Cu is capable of interacting relatively strongly with acidic acetylenic compounds, and traces amounts of the acetylenic compounds left in olefins may be selectively and effectively removed. Here, Cu serves to optimize the location of the sulfonate ligand such that the sulfonate ligand may better interact with the acetylenic compounds.

The organometallic compounds represented by Chemical Formulae (1) to (3) according to the present disclosure may be prepared by reacting a copper halide represented by Chemical Formula (5) with the compounds represented by Chemical Formulae Chemical Formula (6) to (8) according to Schemes 1 to 3:

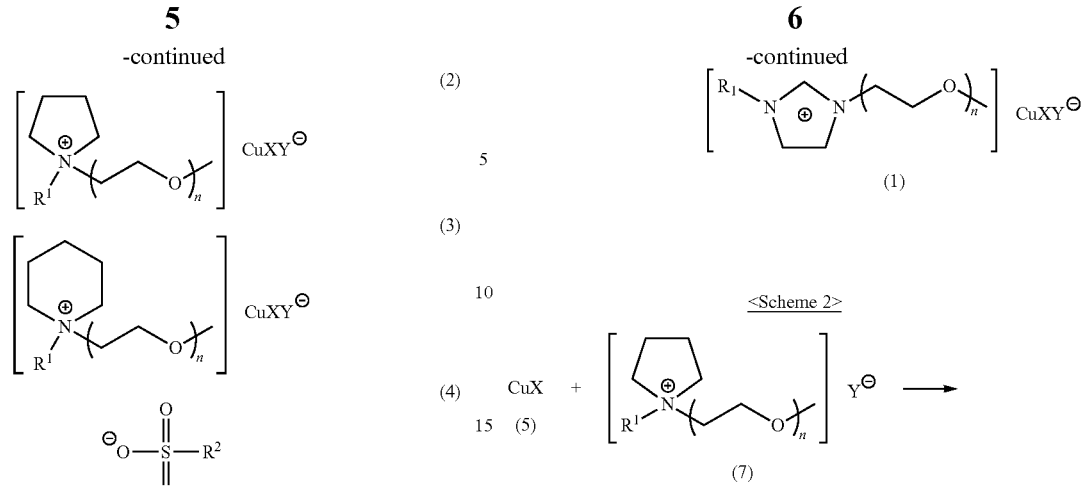

According to an embodiment of the present disclosure, 5 to 30 wt %, specifically 10 to 30 wt %, of CuX represented by Chemical Formula (5) may react based on the compound represented by Chemical Formula Chemical Formula (6), (7) or (8). If the amount of CuX is too small, acetylenic compounds may not be removed effectively. And, if the amount of CuX is too large, the viscosity of the absorbed solution increases, which is unfavorable for processing.

In accordance with the present disclosure, acetylenic compounds may be removed from an olefin mixture using an ionic liquid comprising one or more organometallic compound(s) represented by Chemical Formula (1), (2) or (3).

According to an embodiment of the present disclosure, the amount of the olefin mixture may be 0.2 to 5 times, specifically 0.5 to 2 times, of the ionic liquid having ether groups based on weight. Although the amount may be larger or smaller, a small amount of olefin based on the ionic liquid solution is unfavorable in productivity and an excessive amount may result in decreasing the removal efficiency of acetylenic compounds, which necessitates a multi-step absorption or extraction process.

The removal of acetylenes in olefin using the ionic liquid solution comprising the Cu(I) compound according to the present disclosure may be carried out by absorption or extraction. An absorption process is favorable if the olefin is in the gas phase, and energy consumption may be minimized by employing an extraction process if it is in the liquid phase.

The ionic liquid according to the present disclosure can be used to remove $C_2$-$C_5$ acetylenic compounds, such as acetylene, methylacetylene, ethylacetylene and isopropylacetylene, from the olefin mixture. For $C_2$-$C_4$ olefins, which exist as gas at normal temperature, an absorption process may be employed. And, for olefins of $C_5$ or more, which exist as liquid normal temperature, a liquid extraction process may be employed, or an absorption process may be employed following vaporization. If the olefin mixture is in liquid state, the ionic liquid containing acetylene may be easily separated from the olefin compound through layer separation.

In an embodiment of the present disclosure, the reaction, i.e. the absorption or extraction, may be performed at 0 to 100° C., specifically at 20 to 50° C. If the reaction temperature is below 20° C. or above 50° C., undesired energy consumption may increase.

Oonic liquid according to the present disclosure may be regenerated after the acetylenic compounds are removed from the olefin mixture. Following the absorption or extraction process, the ionic liquid solution may be regenerated at 50 to 200° C., specifically at 80 to 200° C., although the regeneration temperature may be different depending on the degassing condition. If the regeneration temperature is below 80° C., the regeneration efficiency may decrease. And, if it is above 200° C., the ionic liquid having ether groups represented by Chemical Formula (1), (2) or (3) may be partly decomposed.

According to an embodiment of the present disclosure, degassing may be performed in a vacuum of about 1 to 200 mmHg, specifically in 50 to 100 mmHg, in industrial aspects. A pressure higher than 100 mmHg may be unfavorable in degassing performance. And, a pressure lower than 50 mmHg may be unfavorable in energy consumption.

EXAMPLES

The examples and experiments will now be described. The following examples and experiments are only for illustrative purposes and not intended to limit the scope of this disclosure.

Example 1

Synthesis of Ionic Liquids Having Ether Groups

Imidazolium-, pyrrolidinium- and piperidinium-based ionic liquids having ether groups were synthesized in two stages. First, 1-methylimidazole and a glycol having ether group(s) were reacted with an alkanesulfonyl chloride to synthesize an ether-substituted sulfonate intermediate. Then, the sulfonate intermediate was reacted with 1-alkylimidazole, 1-alkylpyrrolidinone or 1-alkylpiperidine to prepare an ionic liquid having ether group(s).

Example 1-(1)

Synthesis of Ethylene Glycol Monomethyl Ether Methanesulfonate

1-Methylimidazole (50 g) and methanesulfonyl chloride (66 g) were mixed in dichloromethane in a 500 mL two-bulb flask. After adding ethylene glycol monomethyl ether (42 g) dropwise at 10° C., the mixture was stirred at room temperature for 4 hours. After the reaction was completed, water was added. After stirring for 10 minutes, the solvent layer in which the product was dissolved was separated from the aqueous layer in which the byproduct was dissolved. The product was yielded by removing the solvent at room temperature using an evaporator (yield: 980), and the byproduct 1-methylimidazolium chloride was recovered as 1-methylimidazole using 40 wt % NaOH aqueous solution and used again (yield: 95%).

Other ether-substituted sulfonate intermediates were synthesized in a similar manner.

Example 1-(2)

Synthesis of 1-ethylene glycol monomethyl ether 3-methylimidazolium methanesulfonate 1-Methylimidazole (40 g) and ethylene glycol monomethyl ether methanesulfonate (90 g) were stirred at 80° C. for 12 hours in benzene in a 500 mL two-bulb flask equipped with a reflux condenser. After the reaction was completed, the product was washed several times with ethyl acetate or diethyl ether to remove unreacted 1-methylimidazole and ethylene glycol monomethyl ether methanesulfonate. The remaining ionic liquid was dried at 60° C. in vacuum (yield: 96%).

Other imidazolium-based ionic liquids having ether groups were synthesized in a similar manner.

Example 1-(3)

Synthesis of 1-diethylene glycol monomethyl ether 1-methylpyrrolidinium ethanesulfonate 1-Methylpyrrolidine (40 g) and 1-diethylene glycol monomethyl ether ethanesulfonate (120 g) were stirred at 80° C. for 12 hours in benzene in a 500 mL two-bulb flask equipped with a reflux condenser. After the reaction was completed, the product was washed several times with ethyl acetate or diethyl ether to remove unreacted 1-methylpyrrolidine and 1-diethylene glycol monomethyl ether ethanesulfonate. The remaining ionic liquid was dried at 60° C. in vacuo (yield: 970).

Other pyrrolidinium-based ionic liquids having ether groups were synthesized in a similar manner.

Example 1-(4)

Synthesis of 1-triethylene glycol monomethyl ether 1-butylpiperidinium methanesulfonate 1-Butylpiperidine (60 g) and 1-triethylene glycol monomethyl ether methanesulfonate (124 g) were stirred at 80° C. for 12 hours in benzene solvent in a 500 mL two-bulb flask equipped with a reflux condenser. After the reaction was completed, the product was washed several times with ethyl acetate or diethyl ether to remove unreacted 1-butylpiperidine and 1-triethylene glycol monomethyl ether methanesulfonate. The remaining ionic liquid was dried at 60° C. in a vacuum (yield: 98%).

Other piperidinium-based ionic liquids having ether groups were synthesized in a similar manner.

Examples 2 to 120

Removal of Acetylenic Compounds

Example 2

An isoprene sample (1 g) containing a $C_5$ acetylenic compound isopropylacetylene (IPA) and 2-butyne (2-BT), 1,000 ppm each, as well as 5,000 ppm n-heptane by internal standard was mixed at 25° C. with an ionic liquid solution of CuCl (0.4 g) dissolved in an imidazolium-based ionic liquid having 1-alkyl ether group(s) (1-hexaethylene glycol monomethyl ether 3-butylimidazolium butanesulfonate, 2.0 g). After stirring 1 minute, the upper and lower layers were subjected to compositional analysis by GC and $^1$H NMR. It was revealed that 100% of IPA, 37% of 2-BT and 0.05% of isoprene were extracted to the ionic liquid solution layer. For the compositional analysis, Agilent's GC system (model 6890N) equipped with HP-PLOT column and Brucker's 400 MHz NMR system were used.

Example 3

An isoprene sample (1 g) containing a $C_5$ acetylenic compound IPA and 2-BT, 1,000 ppm each, as well as 5,000 ppm n-heptane by internal standard was mixed at 25° C. with an ionic liquid solution of CuCl (0.4 g) dissolved in an pyrrolidinium-based ionic liquid having 1-alkyl ether group(s) (1-diethylene glycol monomethyl ether 1-ethylpyrrolidinium ethanesulfonate, 2.0 g). After stirring for 1 minute, the upper and lower layers were subjected to compositional analysis by GC and $^1$H NMR. It was revealed that 100% of IPA, 41% of 2-BT and 0.06% of isoprene were extracted to the ionic liquid solution layer. For the compositional analysis, Agilent's GC system (model 6890N) equipped with HP-PLOT column and Brucker's 400 MHz NMR system were used.

Example 4

An isoprene sample (1 g) containing a $C_5$ acetylenic compound IPA and 2-BT, 1,000 ppm each, as well as 5,000 ppm n-heptane by internal standard was mixed at 25° C. with an ionic liquid solution of CuCl (0.4 g) dissolved in an piperidinium-based ionic liquid having 1-alkyl ether group(s) (1-hexaethylene glycol monomethyl ether 3-butylpiperidinium butanesulfonate, 2.0 g). After stirring for 1 minute, the upper and lower layers were subjected to compositional analysis by GC and $^1$H NMR. It was revealed that 100% of IPA, 46% of 2-BT and 0.08% of isoprene were extracted to the ionic liquid solution layer. For the compositional analysis, Agilent's GC system (model 6890N) equipped with HP-PLOT column and Brucker's 400 MHz NMR system were used.

Examples 5 to 10

Solutions were prepared using imidazolium-based ionic liquids having 1-alkyl ether groups represented by Chemical Formula (1) and extraction experiments were carried out in the same manner as Example 2. The result is given in Table 1.

TABLE 1

| | Ionic liquid | | | | Acetylene removal rate (%) | |
|---|---|---|---|---|---|---|
| Example | $R^1$ | $R^2$ | n | $Y^-$ | IPA | 2-BT |
| 5 | $CH_3$ | $CH_3$ | 1 | $H_3CSO_3$ | 100 | 32 |
| 6 | $CH_3$ | $C_2H_5$ | 2 | $H_5C_2SO_3$ | 100 | 34 |
| 7 | $C_4H_9$ | $CH_3$ | 3 | $H_3CSO_3$ | 100 | 34 |
| 8 | $CH_3$ | $C_3H_7$ | 4 | $H_7C_3SO_3$ | 100 | 35 |
| 9 | $C_2H_5$ | $C_2H_5$ | 5 | $H_5C_2SO_3$ | 100 | 36 |
| 10 | $C_4H_9$ | $C_4H_9$ | 6 | $H_9C_4SO_3$ | 100 | 37 |

IPA: isopropenylacetylene
2-BT: 2-butyne

Examples 11 to 16

Solutions were prepared using pyrrolidinium-based ionic liquids having 1-alkyl ether groups represented by Chemical Formula (2) and extraction experiments were carried out in the same manner as Example 3. The result is given in Table 2.

TABLE 2

| | Ionic liquid | | | | Acetylene removal rate (%) | |
|---|---|---|---|---|---|---|
| Example | $R^1$ | $R^2$ | n | $Y^-$ | IPA | 2-BT |
| 11 | $CH_3$ | $CH_3$ | 1 | $H_3CSO_3$ | 100 | 37 |
| 12 | $CH_3$ | $C_2H_5$ | 2 | $H_5C_2SO_3$ | 100 | 38 |
| 13 | $C_4H_9$ | $CH_3$ | 3 | $H_3CSO_3$ | 100 | 38 |
| 14 | $CH_3$ | $C_3H_7$ | 4 | $H_7C_3SO_3$ | 100 | 39 |
| 15 | $C_2H_5$ | $C_2H_5$ | 5 | $H_5C_2SO_3$ | 100 | 41 |
| 16 | $C_4H_9$ | $C_4H_9$ | 6 | $H_9C_4SO_3$ | 100 | 41 |

IPA: isopropenylacetylene
2-BT: 2-butyne

Examples 17 to 22

Solutions were prepared using piperidinium-based ionic liquids having 1-alkyl ether groups represented by Chemical Formula (3) and extraction experiments were carried out in the same manner as Example 4. The results are given in Table 3.

TABLE 2

| | Ionic liquid | | | | Acetylene removal rate (%) | |
|---|---|---|---|---|---|---|
| Example | $R^1$ | $R^2$ | n | $Y^-$ | IPA | 2-BT |
| 11 | $CH_3$ | $CH_3$ | 1 | $H_3CSO_3$ | 100 | 37 |
| 12 | $CH_3$ | $C_2H_5$ | 2 | $H_5C_2SO_3$ | 100 | 38 |
| 13 | $C_4H_9$ | $CH_3$ | 3 | $H_3CSO_3$ | 100 | 38 |
| 14 | $CH_3$ | $C_3H_7$ | 4 | $H_7C_3SO_3$ | 100 | 39 |
| 15 | $C_2H_5$ | $C_2H_5$ | 5 | $H_5C_2SO_3$ | 100 | 41 |
| 16 | $C_4H_9$ | $C_4H_9$ | 6 | $H_9C_4SO_3$ | 100 | 41 |

IPA: isopropenylacetylene
2-BT: 2-butyne

Examples 23 to 28

Solutions were prepared by varying the amount of CuCl based on the imidazolium-based ionic liquids having ether groups and extraction experiments were carried out in the same manner as Example 2. The results are given in Table 4.

TABLE 4

| Example | wt. % (CuCl/IL)* | Acetylene removal rate (%) | |
|---|---|---|---|
| | | IPA | 2-BT |
| 23 | 5 | 87 | 26 |
| 24 | 10 | 95 | 30 |
| 25 | 15 | 100 | 33 |
| 26 | 20 | 100 | 37 |
| 27 | 25 | 100 | 40 |
| 28 | 30 | 100 | 43 |

*IL: 1-hexaethylene glycol monomethyl ether 3-butylimidazolium butanesulfonate

Examples 29 to 34

Solutions were prepared by varying the amount of CuCl based on the pyrrolidinium-based ionic liquids having ether groups and extraction experiments were carried out in the same manner as Example 3. The results are given in Table 5.

TABLE 5

| Example | wt. % (CuCl/IL)* | Acetylene removal rate (%) | |
|---|---|---|---|
| | | IPA | 2-BT |
| 29 | 5 | 91 | 28 |
| 30 | 10 | 98 | 31 |
| 31 | 15 | 100 | 36 |
| 32 | 20 | 100 | 41 |
| 33 | 25 | 100 | 45 |
| 34 | 30 | 100 | 49 |

*IL: 1-diethylene glycol monomethyl ether 1-ethylpyrrolidinium ethane sulfonate

Examples 35 to 40

Solutions were prepared by varying the amount of CuCl based on the piperidinium-based ionic liquids having ether groups and extraction experiments were carried out in the same manner as Example 4. The results are given in Table 6.

TABLE 6

| Example | wt. % (CuCl/IL)* | Acetylene removal rate (%) | |
|---|---|---|---|
| | | IPA | 2-BT |
| 35 | 5 | 94 | 33 |
| 36 | 10 | 100 | 37 |
| 37 | 15 | 100 | 41 |
| 38 | 20 | 100 | 46 |
| 39 | 25 | 100 | 49 |
| 40 | 30 | 100 | 53 |

*IL: 1-hexaethylene glycol monomethyl ether 3-butylpiperidinium butanesulfonate

Examples 41 and 42

Solutions were prepared by varying CuX and extraction experiments were carried out in the same manner as Example 2. The results are given in Table 7.

TABLE 7

| Example | CuX | Acetylene removal rate (%) | |
|---|---|---|---|
| | | IPA | 2-BT |
| 41 | CuBr | 100 | 40 |
| 42 | CuI | 100 | 42 |

Examples 43 and 44

Solutions were prepared by varying CuX and extraction experiments were carried out in the same manner as Example 3. The results are given in Table 8.

TABLE 8

| Example | CuX | Acetylene removal rate (%) | |
|---|---|---|---|
| | | IPA | 2-BT |
| 43 | CuBr | 100 | 45 |
| 44 | CuI | 100 | 48 |

Examples 45 and 46

Solutions were prepared by varying CuX and extraction experiments were carried out in the same manner as Example 4. The results are given in Table 9.

TABLE 9

| Example | CuX | Acetylene removal rate (%) | |
|---|---|---|---|
| | | IPA | 2-BT |
| 45 | CuBr | 100 | 49 |
| 46 | CuI | 100 | 53 |

Examples 47 to 49

Solutions were prepared using two imidazolium-based ionic liquids A and B (1.0 g each) having different ether groups instead of 2.0 g of 1-hexaethylene glycol monomethyl ether 3-butylimidazolium butanesulfonate and extraction experiments were carried out in the same manner as Example 2. The results are given in Table 10.

TABLE 10

| | Imidazolium-based ionic liquid | | Acetylene removal rate (%) | |
|---|---|---|---|---|
| Example | A | B | IPA | 2-BT |
| 47 | 1-diethylene glycol monomethyl ether 3-propylimidazolium ethanesulfonate | 1-pentaethylene glycol monomethyl ether 3-butylimidazolium butanesulfonate | 100 | 37 |
| 48 | 1-triethylene glycol monomethyl ether 3-butylimidazolium butanesulfonate | 1-tetraethylene glycol monomethyl ether 3-ethylimidazolium methanesulfonate | 100 | 37 |
| 49 | 1-hexaethylene glycol monomethyl ether 3-methylimidazolium propanesulfonate | 1-triethylene glycol monomethyl ether 3-butylimidazolium butanesulfonate | 100 | 38 |

Examples 50 to 52

Solutions were prepared using two pyrrolidinium-based ionic liquids A and B (1.0 g each) having different 1-alkyl ether groups instead of 2.0 g of 1-diethylene glycol monomethyl ether 1-ethylpyrrolidinium ethane sulfonate and extraction experiments were carried out in the same manner as Example 3. The results are given in Table 11.

TABLE 11

| | Pyrrolidinium-based ionic liquid | | Acetylene removal rate (%) | |
|---|---|---|---|---|
| Example | A | B | IPA | 2-BT |
| 50 | 1-diethylene glycol monomethyl ether 3-propylpyrrolidinium ethanesulfonate | 1-pentaethylene glycol monomethyl ether 3-butylpyrrolidinium butanesulfonate | 100 | 42 |
| 51 | 1-triethylene glycol monomethyl ether 3-butylpyrrolidinium butanesulfonate | 1-tetraethylene glycol monomethyl ether 3-ethylpyrrolidinium methanesulfonate | 100 | 43 |
| 52 | 1-hexaethylene glycol monomethyl ether 3-methylpyrrolidinium propanesulfonate | 1-triethylene glycol monomethyl ether 3-butylpyrrolidinium butanesulfonate | 100 | 43 |

Examples 53 to 55

Solutions were prepared using two piperidinium-based ionic liquids A and B (1.0 g each) having different 1-alkyl ether groups instead of 2.0 g of 1-hexaethylene glycol monomethyl ether 3-butylpiperidinium butanesulfonate and extraction experiments were carried out in the same manner as Example 4. The results are given in Table 12.

TABLE 12

| | Piperidinium-based ionic liquid | | Acetylene removal rate (%) | |
|---|---|---|---|---|
| Example | A | B | IPA | 2-BT |
| 53 | 1-diethylene glycol monomethyl ether 3-propylpiperidinium ethanesulfonate | 1-pentaethylene glycol monomethyl ether 3-butylpiperidinium butanesulfonate | 100 | 46 |
| 54 | 1-triethylene glycol monomethyl ether 3-butylpiperidinium butanesulfonate | 1-tetraethylene glycol monomethyl ether 3-ethylpiperidinium methanesulfonate | 100 | 47 |
| 55 | 1-hexaethylene glycol monomethyl ether 3-methylpiperidinium propanesulfonate | 1-triethylene glycol monomethyl ether 3-butylpiperidinium butanesulfonate | 100 | 47 |

Examples 56 to 61

Extraction experiments were carried out by varying the sample amount based on the imidazolium-based ionic liquid having 1-alkyl ether group in Example 2. The results are given in Table 13.

TABLE 13

| | Sample (olefin) amount (g)/ionic | Acetylene removal rate (%) | |
|---|---|---|---|
| Example | liquid amount (g) | IPA | 2-BT |
| 56 | 0.20 | 100 | 54 |
| 57 | 0.50 | 100 | 37 |
| 58 | 1.00 | 97 | 33 |
| 59 | 1.50 | 90 | 29 |
| 60 | 2.00 | 84 | 24 |
| 61 | 5.00 | 78 | 20 |

Examples 62 to 67

Extraction experiments were carried out by varying the sample amount based on the pyrrolidinium-based ionic liquid having 1-alkyl ether group in Example 3. The results are given in Table 14.

TABLE 14

| | Sample (olefin) amount (g)/ionic | Acetylene removal rate (%) | |
|---|---|---|---|
| Example | liquid amount (g) | IPA | 2-BT |
| 62 | 0.20 | 100 | 60 |
| 63 | 0.50 | 100 | 41 |
| 64 | 1.00 | 100 | 38 |
| 65 | 1.50 | 93 | 34 |
| 66 | 2.00 | 87 | 30 |
| 67 | 5.00 | 81 | 24 |

Examples 68 to 73

Extraction experiments were carried out by varying the sample amount based on the piperidinium-based ionic liquid having 1-alkyl ether group in Example 4. The results are given in Table 15.

TABLE 15

| | Sample (olefin) amount (g)/ionic | Acetylene removal rate (%) | |
|---|---|---|---|
| Example | liquid amount (g) | IPA | 2-BT |
| 68 | 0.20 | 100 | 67 |
| 69 | 0.50 | 100 | 46 |
| 70 | 1.00 | 100 | 41 |
| 71 | 1.50 | 96 | 37 |
| 72 | 2.00 | 89 | 32 |
| 73 | 5.00 | 84 | 27 |

Examples 74 to 79

Extraction experiments were carried out by varying the sample and the imidazolium-based ionic liquid having 1-alkyl ether group in Example 2. The results are given in Table 16. The proportion of the imidazolium-based ionic liquid having ether group to CuCl was 20%, and the ethylene, propylene and 1-butene samples included 1,000 ppm of acetylene, methylacetylene and ethylacetylene, respectively.

TABLE 16

| Example | Sample | Ionic liquid | Acetylene removal rate (%) |
|---|---|---|---|
| 74 | ethylene | 1-ethylene glycol monomethyl ether 3-methylimidazolium methanesulfonate | 96 |
| 75 | propylene | 1-diethylene glycol monomethyl ether 3-methylimidazolium ethanesulfonate | 97 |
| 76 | 1-butene | 1-triethylene glycol monomethyl ether 3-propylimidazolium propanesulfonate | 98 |
| 77 | ethylene | 1-tetraethylene glycol monomethyl ether 3-butylimidazolium propanesulfonate | 99 |
| 78 | propylene | 1-pentaethylene glycol monomethyl ether 3-butylimidazolium butanesulfonate | 100 |
| 79 | 1-butene | 1-hexaethylene glycol monomethyl ether 3-butylimidazolium butanesulfonate | 100 |

Examples 80 to 85

Extraction experiments were carried out by varying the sample and the pyrrolidinium-based ionic liquid having 1-alkyl ether group in Example 3. The results are given in Table 17. The proportion of the pyrrolidinium-based ionic liquid having ether group to CuCl was 20%, and the ethylene, propylene and 1-butene samples included 1,000 ppm of acetylene, methylacetylene and ethylacetylene, respectively.

TABLE 17

| Example | Sample | Ionic liquid | Acetylene removal rate (%) |
|---|---|---|---|
| 80 | ethylene | 1-ethylene glycol monomethyl ether 3-methylpyrrolidinium methanesulfonate | 98 |
| 81 | propylene | 1-diethylene glycol monomethyl ether 3-methylpyrrolidinium ethanesulfonate | 98 |
| 82 | 1-butene | 1-triethylene glycol monomethyl ether 3-propylpyrrolidinium propanesulfonate | 99 |
| 83 | ethylene | 1-tetraethylene glycol monomethyl ether 3-butylpyrrolidinium propanesulfonate | 100 |
| 84 | propylene | 1-pentaethylene glycol monomethyl ether 3-butylpyrrolidinium butanesulfonate | 100 |
| 85 | 1-butene | 1-hexaethylene glycol monomethyl ether 3-butylpyrrolidinium butanesulfonate | 100 |

Examples 86 to 91

Extraction experiments were carried out by varying the sample and the piperidinium-based ionic liquid having 1-alkyl ether group in Example 4. The results are given in Table 18. The proportion of the piperidinium-based ionic liquid having ether group to CuCl was 20%, and the ethylene, propylene and 1-butene samples included 1,000 ppm of acetylene, methylacetylene and ethylacetylene, respectively.

TABLE 18

| Example | Sample | Ionic liquid | Acetylene removal rate (%) |
|---|---|---|---|
| 86 | ethylene | 1-ethylene glycol monomethyl ether 3-methylpiperidinium methanesulfonate | 99 |
| 87 | propylene | 1-diethylene glycol monomethyl ether 3-methylpiperidinium ethanesulfonate | 99 |
| 88 | 1-butene | 1-triethylene glycol monomethyl ether 3-propylpiperidinium propanesulfonate | 100 |
| 89 | ethylene | 1-tetraethylene glycol monomethyl ether 3-butylpiperidinium propanesulfonate | 100 |
| 90 | propylene | 1-pentaethylene glycol monomethyl ether 3-butylpiperidinium butanesulfonate | 100 |
| 91 | 1-butene | 1-hexaethylene glycol monomethyl ether 3-butylpiperidinium butanesulfonate | 100 |

Examples 92 to 96

Extraction experiments were carried out in the same manner as Example 2 while varying the extraction temperature. The results are given in Table 19.

TABLE 19

| | Extraction temperature | Acetylene removal rate (%) | |
|---|---|---|---|
| Example | (° C.) | IPA | 2-BT |
| 92 | 20 | 100 | 42 |
| 93 | 25 | 100 | 37 |
| 94 | 30 | 97 | 34 |
| 95 | 40 | 92 | 31 |
| 96 | 50 | 85 | 28 |

Examples 97 to 101

Extraction experiments were carried out in the same manner as Example 3 while varying the extraction temperature. The results are given in Table 20.

TABLE 20

| | Extraction temperature | Acetylene removal rate (%) | |
|---|---|---|---|
| Example | (° C.) | IPA | 2-BT |
| 97 | 20 | 100 | 47 |
| 98 | 25 | 100 | 41 |
| 99 | 30 | 98 | 37 |
| 100 | 40 | 94 | 34 |
| 101 | 50 | 90 | 30 |

Examples 102 to 106

Extraction experiments were carried out in the same manner as Example 4 while varying the extraction temperature. The results are given in Table 21.

TABLE 21

| Example | Extraction temperature (° C.) | Acetylene removal rate (%) | |
|---|---|---|---|
| | | IPA | 2-BT |
| 102 | 20 | 100 | 50 |
| 103 | 25 | 100 | 46 |
| 104 | 30 | 100 | 41 |
| 105 | 40 | 96 | 36 |
| 106 | 50 | 92 | 33 |

Examples 107 to 111

After performing extraction experiments in the same manner as Example 2, hydrocarbons (olefin and acetylene) extracted in the imidazolium-based ionic liquid solution having ether group were degassed under reduced pressure. The results are given in Table 22.

TABLE 22

| Example | Degassing temperature (° C.) | Degassing pressure (mmHg) | Degassing rate (%) | |
|---|---|---|---|---|
| | | | IPA | 2-BT |
| 107 | 20 | 50 | 87 | 92 |
| 108 | 50 | 20 | 100 | 100 |
| 109 | 50 | 70 | 96 | 98 |
| 110 | 70 | 50 | 100 | 100 |
| 111 | 100 | 100 | 100 | 100 |

Examples 112 to 116

After performing extraction experiments in the same manner as Example 3, hydrocarbons (olefin and acetylene) extracted in the pyrrolidinium-based ionic liquid solution having ether group were degassed under reduced pressure. The results are given in Table 23.

TABLE 23

| Example | Degassing temperature (° C.) | Degassing pressure (mmHg) | Degassing rate (%) | |
|---|---|---|---|---|
| | | | IPA | 2-BT |
| 112 | 20 | 50 | 89 | 95 |
| 113 | 50 | 20 | 100 | 100 |
| 114 | 50 | 70 | 96 | 98 |
| 115 | 70 | 50 | 100 | 100 |
| 116 | 100 | 100 | 100 | 100 |

Examples 117 to 121

After performing extraction experiments in the same manner as Example 4, hydrocarbons (olefin and acetylene) extracted in the piperidinium-based ionic liquid solution having ether group were degassed under reduced pressure. The results are given in Table 24.

TABLE 24

| Example | Degassing temperature (° C.) | Degassing pressure (mmHg) | Degassing rate (%) | |
|---|---|---|---|---|
| | | | IPA | 2-BT |
| 117 | 20 | 50 | 93 | 98 |
| 118 | 50 | 20 | 100 | 100 |
| 119 | 50 | 70 | 100 | 100 |
| 120 | 70 | 50 | 100 | 100 |
| 121 | 100 | 100 | 100 | 100 |

Comparative Example

To compare thermal stability of the ionic liquid having ether group to one having no ether group according to the present disclosure, thermogravimetric analysis (TGA) was carried out for each ionic liquid. The results are shown in FIG. 1.

In FIGS. 1, A and B are the results of the ionic liquids of Example 1-(2). Specifically, A is for 1-triethylene glycol monoethyl ether 3-methylimidazolium methanesulfonate, and B is for 1-ethylene glycol monoethyl ether 3-methylimidazolium methanesulfonate. C is the result for 1,3-dimethylimidazolium methylphosphite ([Dimm]MeHPO$_3$) as the ionic liquid having no ether group. It can be seen from the graphs that the ionic liquids A and B according to the present disclosure have much superior thermal stability than the ionic liquid C having no ether group.

When a solution of the imidazolium-, pyrrolidinium- or piperidinium-based ionic liquid having ether group(s) wherein CuX (X=Cl, Br, I) is dissolved according to the present disclosure is used to remove acetylenes in olefin by absorption or extraction, oxidation of Cu(I) to Cu(II) is prevented since CuX is stabilized by the ionic liquid. Thus, selective removal efficiency of acetylenic compounds is improved greatly while the removal performance is retained for a long period of time. Further, since the solution according to the present disclosure is in the liquid state, absorption or extraction processes are applicable, which are much less costly than adsorption or membrane separation processes. In addition, as the imidazolium-, pyrrolidinium- or piperidinium-based ionic liquid solution having ether group(s) according to the present disclosure has very low vapor pressure, material loss is very small compared to existing absorbents or extractants, and the process is much simpler than when an absorbent or adsorbent in a slurry form is used.

While the present disclosure has been described with respect to the specific embodiments, it will be apparent to those skilled in the art that various changes and modifications may be made without departing from the spirit and scope of the disclosure as defined in the following claims.

What is claimed is:

1. An ionic liquid comprising one or more organometallic compound(s) represented by Chemical Formula (1), (2) or (3):

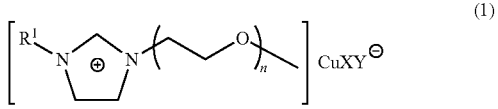

-continued

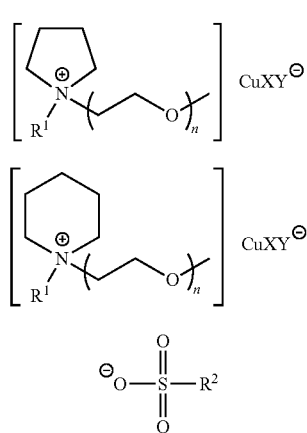

wherein
X is an anion selected from Cl, Br and I,
R¹ is $C_1$-$C_4$ substituted or unsubstituted alkyl,
n is an integer from 1 to 6, and
Y is a sulfonate anion represented by Chemical Formula (4), wherein $R^2$ is $C_1$-$C_4$ substituted or unsubstituted alkyl.

2. A method for preparing an organometallic compound represented by Chemical Formula (1), comprising reacting a copper halide represented by Chemical Formula (5) with a compound represented by Chemical Formula (6) according to Scheme 1:

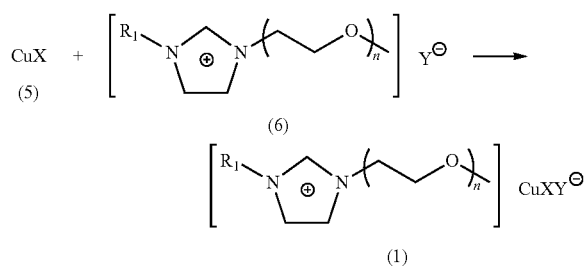

wherein
X is an anion selected from Cl, Br and I,
R¹ is $C_1$-$C_4$ substituted or unsubstituted alkyl,
n is an integer from 1 to 6, and
Y is a sulfonate anion represented by Chemical Formula (4):

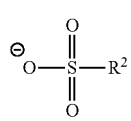

wherein $R^2$ is $C_1$-$C_4$ substituted or unsubstituted alkyl.

3. A method for preparing an organometallic compound represented by Chemical Formula (2), comprising reacting a copper halide represented by Chemical Formula (5) with a compound represented by Chemical Formula (7) according to Scheme 2:

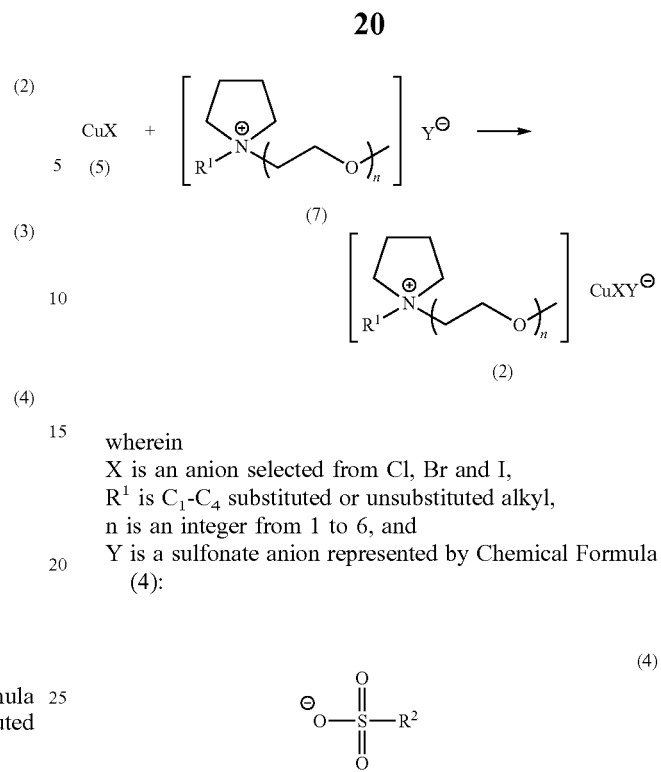

wherein
X is an anion selected from Cl, Br and I,
R¹ is $C_1$-$C_4$ substituted or unsubstituted alkyl,
n is an integer from 1 to 6, and
Y is a sulfonate anion represented by Chemical Formula (4):

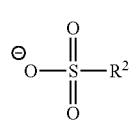

wherein $R^2$ is $C_1$-$C_4$ substituted or unsubstituted alkyl.

4. A method for preparing an organometallic compound represented by Chemical Formula (3), comprising reacting a copper halide represented by Chemical Formula (5) with a compound represented by Chemical Formula (8) according to Scheme 3:

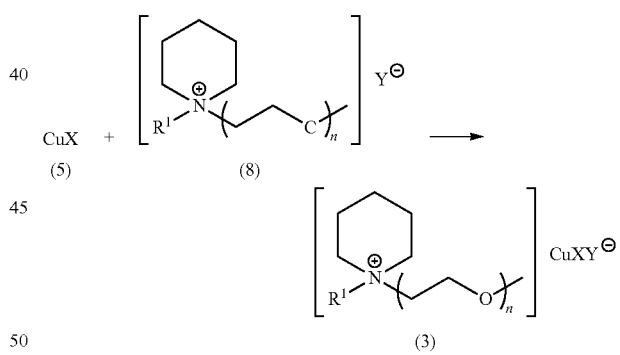

wherein
X is an anion selected from Cl, Br and I,
R¹ is $C_1$-$C_4$ substituted or unsubstituted alkyl,
n is an integer from 1 to 6, and
Y is a sulfonate anion represented by Chemical Formula (4):

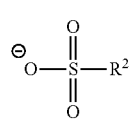

wherein $R^2$ is $C_1$-$C_4$ substituted or unsubstituted alkyl.

5. The method for preparing an organometallic compound according to claim 2, comprising reacting 5 to 30 wt % of the copper halide represented by Chemical Formula (5) based on the compound represented by Chemical Formula Chemical Formula (6).

6. The method for preparing an organometallic compound according to claim 3, comprising reacting 5 to 30 wt % of the copper halide represented by Chemical Formula (5) based on the compound represented by Chemical Formula Chemical Formula (7).

7. The method for preparing an organometallic compound according to claim 4, comprising reacting 5 to 30 wt % of the copper halide represented by Chemical Formula (5) based on the compound represented by Chemical Formula Chemical Formula (8).

* * * * *